(12) United States Patent
Gamm et al.

(10) Patent No.: US 11,992,272 B2
(45) Date of Patent: May 28, 2024

(54) OPTICAL TRACKING DEVICE WITH OPTICALLY DISTINGUISHABLE LINES

(71) Applicant: Stryker European Operations Holdings LLC, Kalamazoo, MI (US)

(72) Inventors: Gerd Ulrich Gamm, Freiburg (DE); Emeric Umbdenstock, Freiburg (DE); Reinhold Zimmermann, Freiburg (DE); Fabian Riegelsberger, Umkirch (DE); Florian Herrmann, Schwanau (DE); Jochen Breisacher, Teningen (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 165 days.

(21) Appl. No.: 16/745,660

(22) Filed: Jan. 17, 2020

(65) Prior Publication Data
US 2020/0229874 A1    Jul. 23, 2020

(30) Foreign Application Priority Data

Jan. 22, 2019 (EP) .................................. 19153075
May 22, 2019 (EP) .................................. 19175876

(51) Int. Cl.
*A61B 34/20* (2016.01)
*A61B 17/34* (2006.01)
*A61B 17/70* (2006.01)

(52) U.S. Cl.
CPC .......... *A61B 34/20* (2016.02); *A61B 17/3403* (2013.01); *A61B 17/7002* (2013.01);
(Continued)

(58) Field of Classification Search
USPC ....................................................... 600/424
See application file for complete search history.

(56) References Cited

U.S. PATENT DOCUMENTS

| 3,700,313 A | 10/1972 | Karr et al. |
| 5,456,017 A | 10/1995 | Meier |

(Continued)

FOREIGN PATENT DOCUMENTS

| DE | 29521305 U1 | 12/1996 |
| DE | 29622630 U1 | 3/1997 |

(Continued)

OTHER PUBLICATIONS

English language abstract and machine-assisted English translation for DE 295 21 305 extracted from espacenet.com database on Jan. 16, 2020, 20 pages.

(Continued)

*Primary Examiner* — Jason M Ip
*Assistant Examiner* — Renee C Langhals
(74) *Attorney, Agent, or Firm* — Howard & Howard Attorneys PLLC

(57) ABSTRACT

An optical tracking device, a surgical navigation system and a surgical navigation method are disclosed. The optical tracking device comprises a body having at least two optically distinguishable lines, wherein at least one of the lines is an edge of the body. The lines are configured to be detected by an optical detection system simultaneously. They have a fixed spatial relationship between each other. The method comprises providing the optical tracking device, acquiring data describing the fixed spatial relationship, detecting the lines and determining the spatial position and/or orientation of the optical tracking device based on the detected lines and the fixed spatial relationship.

19 Claims, 5 Drawing Sheets

(52) U.S. Cl.
CPC ............. *A61B 2034/2055* (2016.02); *A61B 2034/2057* (2016.02)

(56) References Cited

U.S. PATENT DOCUMENTS

| | | | |
|---|---|---|---|
| 5,897,491 | A | 4/1999 | Kastenbauer et al. |
| 6,328,736 | B1 | 12/2001 | Mulier et al. |
| 6,336,904 | B1 | 1/2002 | Nikolchev |
| RE39,102 | E | 5/2006 | Schulz et al. |
| 7,444,178 | B2 | 10/2008 | Goldbach |
| 8,320,612 | B2 | 11/2012 | Knobel et al. |
| 8,456,649 | B2 | 6/2013 | Maier |
| 9,220,573 | B2 | 12/2015 | Kendrick et al. |
| 9,566,120 | B2 | 2/2017 | Malackowski et al. |
| 2002/0038121 | A1 | 3/2002 | Rozenberg et al. |
| 2004/0002642 | A1 | 1/2004 | Dekel et al. |
| 2004/0138556 | A1* | 7/2004 | Cosman ............. A61B 90/10 600/424 |
| 2006/0285350 | A1* | 12/2006 | Wang ............. G02B 6/001 362/555 |
| 2008/0194973 | A1 | 8/2008 | Imam |
| 2011/0190637 | A1* | 8/2011 | Knobel ............. A61B 34/20 600/476 |
| 2011/0270080 | A1 | 11/2011 | Crane |
| 2013/0106833 | A1* | 5/2013 | Fun ............. G06T 7/73 345/419 |
| 2014/0148820 | A1* | 5/2014 | Ogawa ............. A61B 34/77 606/130 |
| 2015/0327948 | A1 | 11/2015 | Schoepp et al. |

FOREIGN PATENT DOCUMENTS

| | | |
|---|---|---|
| EP | 0428637 B1 | 12/1993 |
| EP | 1920730 A2 | 5/2008 |
| WO | 9938449 A1 | 8/1999 |
| WO | 2009049038 A1 | 4/2009 |
| WO | 2011047467 A1 | 4/2011 |
| WO | 2015022100 A1 | 2/2015 |
| WO | 2015048994 A1 | 4/2015 |

OTHER PUBLICATIONS

English language abstract for DE 296 22 630 extracted from espacenet.com database on Jan. 16, 2020, 1 page.
English language abstract for EP 0 428 637 extracted from espacenet.com database on Jan. 16, 2020, 1 page.
English language abstract for EP 1 920 730 A2 extracted from espacenet.com database on Apr. 6, 2023, 1 page.

* cited by examiner

OPTICAL TRACKING DEVICE WITH OPTICALLY DISTINGUISHABLE LINES

PRIORITY CLAIM

This application claims priority under 35 U.S.C. § 119 to European Patent Application No. 19175876.2, filed May 22, 2019, and European Patent Application No. 19153075.7, filed Jan. 22, 2019, the entire contents of each are hereby incorporated by reference.

TECHNICAL FIELD

The present disclosure generally relates to an optical tracking device configured to be used in surgical navigation. Also, a surgical navigation system comprising the tracking device and a surgical navigation method using the tracking device are presented.

BACKGROUND

Many surgical procedures benefit from determining a position and orientation (i.e., a pose) of surgical objects such as surgical tools and a patient. A surgical navigation system allows tracking of a surgical object and calculating a pose of the surgical object relative to registered three-dimensional image data of the patient.

In a typical application of a surgical navigation system, a surgical tool and the patient are each associated with (for example spatially fixed to) a tracking device, wherein three-dimensional image data previously obtained by, for example, a CT scan is registered with the patient tracking device. By tracking the patient and the surgical tool, the surgical navigation system may determine the pose of both surgical objects and calculate a spatial relationship between the surgical tool and the three-dimensional image data. The determined spatial relationship can, for example, be displayed on a screen, helping the surgeon guide the surgical tool relative to the patient.

A common type of a surgical navigation system comprises an optical detection system comprising an optical sensor that senses light emitted by the tracking device. As light sources, light emitting diodes (LEDs) are often used due to their high efficiency and ability to generate small light spots. In order to determine the pose of the tracking device, a plurality of light sources need to be detected by the optical sensor, wherein a higher degree of freedom requires a larger number of light sources.

However, an optical sensor may only track the device when its LEDs are facing in its direction. When the tracking device is turned and moved away from the optical detection system, at one point the LEDs may no longer be detected and therefore tracking is no longer possible. This loss of tracking may occur during a surgery and therefore should be prevented.

One solution to the problem would be to use a passive optical tracking device with reflective spheres. These reflective spheres have better visibility angles. However, the reflective spheres are vulnerable to contamination, for example by blood, and exhibit an inferior tracking accuracy compared to active tracking devices.

SUMMARY

There is a need for a tracking device that solves one or more of the aforementioned or other problems.

According to a first aspect, an optical tracking device is provided which comprises a body. The body has at least two optically distinguishable lines configured to be detected by an optical detection system of a surgical navigation system simultaneously, wherein at least one of the lines is an edge of the body. The lines have a fixed spatial relationship between each other.

The optical tracking device may be configured to be coupled to a patient or a surgical instrument, such as a needle, a pointer, a drill, a chisel or to a surgical imaging apparatus, an anatomical patient structure. It may be arranged in a fixed spatial relationship to one or more of the aforementioned. For example, the optical tracking device is fixed to a surgical instrument with a predetermined spatial relationship thereto. In case the position and orientation of the optical tracking device is known, the position and orientation of the surgical instrument may also be determined based on the known position and orientation and based on the predetermined spatial relationship.

The fixed spatial relationship of the lines may be predefined and known to the surgical navigation system. Based on the fixed spatial relationship between the lines, the surgical navigation system will perform its calculations (e.g., for tracking one or both of position and orientation of a patient or a surgical instrument).

The number of lines may be three, four, five, six or more. The number of lines may be smaller than 20, for example smaller than 10. In some variants, one or more of the at least two lines are edges of the body. For example, all the lines may be edges of the body.

The body of the optical tracking device has at least two optically distinguishable lines configured to be detected by an optical detection system of a surgical navigation system simultaneously. Such an optical detection system may comprise a monoscopic or stereoscopic camera. The lines may lie in the surface of the body and for example be edges formed between planar surfaces which surfaces make up the body's surface. Simultaneous detection means that at least parts of each of the lines are visible to the optical detection system at a given time, enabling a detection of each of the lines at the given time, thereby enabling the determination of the position and/or orientation of the optical tracking device at the given time. The lines may therefore have be oriented appropriately. For example, the lines may not be arranged on opposing sides of a cubic body since in this case a simultaneous detection would not be possible for many relative spatial orientations between the optical tracking device and the optical detection system. For some arrangements of the lines, a simultaneous detection is impossible due to the optical detection system having a given field of view. For example, the optical detection system has a predetermined viewing direction. For some arrangements, a line might be covered from the body in the viewing direction so that it cannot be detected simultaneously with other lines which are not covered.

The term "optically distinguishable" can mean that the lines may be identified by an optical detection system since they exhibit different light emitting behaviours than other parts of the optical tracking device. Such other parts of the optical tracking device may be parts (e.g., planar or non-planar surfaces) delimited by or adjacent to the lines.

A light emitting behaviour may comprise at least one of a wavelength of emitted light, an intensity of emitted light (including zero intensity), a power of emitted light, a wavelength spectrum of emitted light, and a temporal pattern of emitted light. The light emitting behaviour may be deductible from an emitted light signal. The individual lines may not only be optically distinguishable from other parts of the optical tracking device, but may also be distinguishable from one another by their light emitting behaviours.

The lines have a fixed spatial relationship between each other, which may for example be described via a translational and a rotational component, for example represented in the form of a matrix. In one example, each of the lines is described by a straight line with a certain length in a reference coordinate system. A line may also be described as an infinite straight line which is defined in the reference coordinate system.

The lines in one example do not lie in a single plane. For example, the lines lie in at least two different planes. This is because in order to determine the spatial position and orientation of the optical tracking device based on the detected lines, several degrees of freedom have to be considered. In case the lines have the same length and intersect one another in the middle, a spatial position and orientation of the optical tracking device may not be determined decisively. In this case, multiple spatial positions and/or orientations of the optical tracking device yielding the same line detection result are possible which leads to ambiguity of the detected spatial position and/or orientation. If the lines do not lie in a single plane and/or do not have the same lengths and/or do not intersect each other at the respective middles, the position and orientation of the optical tracking device may be determined unambiguously.

In some cases, even if the lines do not lie in a single plane, not all degrees of freedom of the optical tracking device may be determined unambiguously. For example, in case of a body having the form of a cube and the lines being three lines which intersect at one of the cube's corners, three different rotational orientations are possible resulting in the same line detection result. An additional line may be detected to prevent any such ambiguity, also in the case of lines which lie in the same plane. Alternatively or additionally, the lines may be configured to be distinguishable from one another. Alternatively or additionally, the lines may have an asymmetrical geometrical relationship to prevent this ambiguity. In the example of a cube, two edges which intersect one another at a corner of the cube may be detected and a further line orthogonal to the other two and not touching this intersection point may additionally be detected. Other variations or combinations are possible in order to determine the position and orientation of the optical tracking device decisively as will be apparent to the person skilled in the art.

At least one of the lines is in one example configured to be optically distinguishable by exhibiting a first light emitting behaviour different from a second light emitting behaviour. The second light emitting behaviour is in this example a light emitting behaviour of an area comprised in the optical tracking device, wherein the area has at least a part of the line as a boundary. The line and/or the area may or may not be an active light source. In this case, the first light emitting behaviour or the second light emitting behaviour corresponds to no light emission.

The first light emitting behaviour differs from the second light emitting behaviour for example in at least one of a light intensity of emitted light, a light wavelength of emitted light and a temporal pattern of emitted light. As noted above, the light emitting behaviour may also correspond to no light emission. For example, the first light emitting behaviour comprises a light emission power of 1 $W/m^2$ whereas a light emission power comprised in the second light emitting behaviour is equal to 0 $W/m^2$, which corresponds to no light emission. In other cases, the light emitting power comprised in the second light emitting behaviour may be equal to 1 $W/m^2$ whilst the light emitting power comprised in the first light emitting behaviour is equal to 0 $W/m^2$ which corresponds to no light emission. Of course, other light emitting power values and other relationships of such values are possible.

Light intensities comprised in different light emitting behaviours may differ from one another. A temporal pattern of emitted light as mentioned above may be generated by a temporal variation in light intensity and/or light wavelength. A wavelength of a light signal may be constant at 850 nm or another value selected from the infrared light range whilst a spectrum of another light signal may not include this wavelength or include this wavelength only with a lower intensity than the first light signal.

In an example, at least one of the lines forms a straight line. All of the lines may form straight lines. For example, at least two of the lines touch or intersect one another. At least three of the lines may touch or intersect one another. The lines which touch or intersect one another have at least one spatial point in common.

The body may be platonic solid or a combination of platonic solids. At least one of the lines may be an edge of the platonic solid. In one example, all of the lines are edges of a platonic solid. The term "platonic solid" shall only describe the geometrical form of the body—the body may not be a "solid" body but may instead be hollow. The body may be a cube, a pyramid, a cuboid, a prism or else.

The optical tracking device in one example further comprises a light emitting element. The light emitting element comprises for example an active electronic light emitting element such as a LED, an infrared LED, a LED array, and OLED or a light bulb. Such an active electronic light emitting element may be electronically controlled to emit a certain light signal. For example, the light intensity may be adjusted using current control. The light wavelength may also be adjusted by choosing one of the LEDs comprised in the LED array to be activated or by providing a suitable wavelength filter. The temporal pattern of emitted light may also be adjusted, for example by varying the current used to activate the active electronic light emitting element. In another example, the light emitting element comprises a luminescent material. Also in this case, wavelength filters and/or light shielding elements may be provided in order to enable control of the light wavelength and/or the temporal pattern of the light signal.

The light emitting element may be embedded inside the optical tracking device. For example, the body of the optical tracking device is a hollow body inside of which the light emitting element is arranged. The light emitting element may also be moulded into or encapsulated in the optical tracking device. The light emitting element may be disposed on the optical tracking device. For example, the light emitting element is arranged on a surface and/or a line of the body of the optical tracking device.

The light emitting element is for example configured to illuminate a part of at least one of the lines. For example, the light-emitting element is configured to illuminate a line segment with a certain length which is part of one of the lines or points which are part of one of the lines. The light-emitting element may be configured to illuminate a complete line or only individual points or sections of different lengths along the line. It may be configured to illuminate all of the lines completely. For example, the light-emitting element is embedded inside the optical tracking device and configured to illuminate all of the lines completely.

In one example, the light emitting element comprises an optical fibre. In this case, the optical fibre might run along the at least one of the lines and be configured to emit light out of a side portion of the fibre. For this purpose, a side-emitting optical fibre such as fibre "12" disclosed in European Patent Application No. 19153075.7, hereby incorporated by reference in its entirety, might be used. For example, the fibre shown in any one of FIGS. 3B to 3C and described in the corresponding passages of the description of the European Patent Application No. 19153075.7 might be used to illuminate a part of at least one of the lines. The light-emitting element comprises a light source configured to couple light into such a fibre. The fibre may run along the line to be illuminated and have the light-emitting portions arranged to the outside of the body of the optical tracking device in order to emit a light signal. The optical fibre may run along more than one line to be illuminated or along all lines to be illuminated. The fibre may then emit light through the light emitting portions at parts of each of these lines. The optical fibre may at least at the light emitting portions be covered with an optically transparent material.

The light emitting element may be configured to illuminate at least one area comprised in the optical tracking device, wherein the area has at least a part of one of the lines as a boundary. For example, the area forms a side of the body. The area may be a part of a surface of the body such as a side surface. For example, the light-emitting element is configured to illuminate a line so that the line exhibits the first light emitting behaviour and an area so that the area exhibits the second light emitting behaviour.

The light-emitting element may be configured to illuminate the line with a full light intensity and illuminate the area with a lower light intensity generated using a filter or blocker, for example. The light-emitting element may be configured to illuminate the line with a given light intensity and not illuminate the area with light by using a filter or blocker, for example. The filter or blocker may form the surface of the body and have the aforementioned illuminated area as the surface.

The light-emitting element may also be configured to illuminate the line with a first temporal light pattern and the area with a second temporal light pattern which is for example anticyclic (inverse) to the first temporal light pattern. For that purpose, switching means may be included in the light emitting element in order to switch illumination between the line and the area. The light emitting element may comprise several light sources, for example one light source for each part of the body which is to be illuminated such as one light source for each line or for each area. The light emitting element may be configured to only illuminate areas comprised in the optical tracking device which have at least a part of one of the lines as a boundary.

In one example, at least one of the lines and/or at least one area is covered with an optically transparent material, wherein the area has at least a part of one of the lines as a boundary. For example, the transparent material is glass, a transparent plastic material, a transparent metal oxide or a transparent ceramic material. For example, the body is made of such a transparent material and parts of the surface are covered with a light-blocking colour or light-blocking elements, sparing the lines and/or areas. In a different example, the body is made of opaque or non-transparent material and only the lines and/or areas are covered with an optically transparent material in order to enable light transmission through the transparent material resulting in light emitted from the lines and/or areas.

According to a second aspect, a surgical navigation system is provided. The surgical navigation system comprises the optical tracking device as presented herein. The surgical navigation system further comprises an optical detection system configured to detect the lines of the optical tracking device simultaneously. For example, the optical detection system is configured to detect at least two of the at least two optically distinguishable lines simultaneously. For example, the optical detection system is configured to detect all of the at least two optically distinguishable lines simultaneously. For example, the optical detection system comprises an optical sensor such as a camera. The optical detection system for example comprises a monoscopic or stereoscopic camera with a given viewing direction and/or field of view. The optical detection system may be able to detect a line as light source instead of just points. It may be able to detect an area as light source instead of just points. For example, the optical tracking device comprises a camera configured to detect several points, a line and/or an area at the same time/simultaneously. The camera may be a stereoscopic camera with two 2D image sensors. Details of the detection of the lines are described with reference to the first and the third aspect and in the detailed description.

Also, the surgical navigation system may comprise a localisation system configured to determine a spatial position and/or orientation of the optical tracking device based on the detected lines and based on the fixed spatial relationship between the at least two optically distinguishable lines. Details of the determination are described with reference to the first and the third aspect and in the detailed description.

The surgical navigation system may be configured to acquire data describing the fixed spatial relationship from a storage unit. For example, a user selects the optical tracking device on a user interface comprised in the surgical navigation system. The surgical navigation system may then acquire data describing the fixed spatial relationship associated to this optical tracking device from the storage unit. The storage unit may be part of the surgical navigation system. It may be part of a remote storage device accessible via a network by the surgical navigation system.

According to a third aspect, a surgical navigation method is provided. The method, for example a surgical navigation method, is a method of determining a spatial position and/or orientation of the optical tracking device. The method may be executed by the surgical navigation system as described above.

The method comprises providing an optical tracking device comprising a body having at least two optically distinguishable lines, wherein at least one of the lines is an edge of the body. For example, the optical tracking device described above is provided.

The method further comprises simultaneously detecting the lines. For example, this means detecting at least two of the at least two optically distinguishable lines. In one variant this means detecting all of the at least two optically distinguishable lines. The detection may be performed by the optical detection system described above.

It also comprises acquiring data describing a fixed spatial relationship between the at least two optically distinguishable lines, for example from the storage unit described above.

Also, the method comprises determining, based on the detected lines and based on the fixed spatial relationship, the spatial position and/or orientation of the optical tracking device.

The step of detecting the lines for example comprises detecting at least one of an illuminated line, an illuminated part of a line and an illuminated area having at least a part of one of the lines as a boundary. For example, two or three illuminated lines are detected. In another example, an illuminated area having a first line as a boundary is detected and a second illuminated line is also detected. In another example, two illuminated areas are detected which are separated by a first line, wherein one of the areas is adjacent to a second illuminated line. A part of a third illuminated line may also be detected. Of course, other combinations are possible. An "illuminated" part in these examples means that this part exhibits a light emitting behaviour comprising a light intensity larger than zero. As noted above, the remaining parts may also be illuminated but optically distinguishable from the aforementioned respective illuminated parts due to the emission of a different light signal resulting in different light emitting behaviours.

In one example, the step of detecting the lines comprises detecting at least one illuminated part of a line and extrapolating and/or interpolating the detected illuminated part to a straight line. This straight line may have a predetermined length which is part of the fixed spatial relationship between the lines. It may have an infinite length. For example, in case several points forming a line (being part of a line/lying on a line) are detected, these points may be interpolated and/or extrapolated to a straight line in order to detect the line. In case one or more line segments with a certain length are detected and the one or more line segments form a line, the segment/s may be interpolated and/or extrapolated to a straight line in order to detect the line. A combination of detected points and line segments forming a line may be interpolated and/or extrapolated to a straight line in order to detect the line. In case the line is not a straight line but a curved line having a form comprised in the fixed spatial relationship between the lines, the detected elements such as points and/or line segments forming the curved line may be interpolated and/or extra-polated to detect the line. For example, only detected elements which lie on a line with the fixed curvature/form are grouped together. The grouped elements are then used to interpolate and/or extrapolate their positions and orientations to a line with the fixed curvature/form in order to detect the line with the fixed curvature/form.

The step of detecting the lines may alternatively or additionally comprise detecting at least one illuminated area having at least a part of one of the lines as a boundary and extrapolating and/or interpolating the boundary of the area to a straight line. For example, a part of the boundary which is a straight segment may be interpolated and/or extrapolated to straight line. Several interpolations and/or extrapolations for several such segments may lead to a plurality of straight lines, some or all of which may be formed by a line of the optical tracking device. For example, each interpolated and/or extrapolated straight line may correspond to a line of the optical tracking device. In order to determine which of the interpolated lines shall be used to determine the position and/or orientation of the optical tracking device, the fixed spatial relationship between the lines may be taken into account. For example, interpolated straight lines which do not fulfil the fixed spatial relationship to any of the other interpolated straight lines may be discarded. In the end, the correct lines may be detected which enables a precise and reliable determination of the position and/or orientation of the optical tracking device. Also in this case, the lines may not be straight but curved. The curvature/form may then be comprised in the fixed spatial relationship between the lines. The interpolation and/or extrapolation then take this into account in order to obtain interpolated and/or extrapolated lines with a given curvature/form in order to detect the lines. For example, only detected boundary segments which lie on a line with the fixed curvature/form are grouped together. The grouped elements are then used to interpolate and/or extrapolate their positions and orientations to a line with the fixed curvature/form in order to detect the line with the fixed curvature/form.

Additionally or alternatively, other methods such as pattern recognition may be used in order to detect a line based on the detection of a point, a line segment or a line.

Also provided is a computer program product comprising program code portions configured to perform the method presented herein when executed by one or more processors. The computer program product may be stored on a, for example non-transitory, computer-readable recording medium, such as a hard disk or a semiconductor memory. Also, the computer program product may be transmitted in the form of a data stream. That is, the data stream may be representative of the computer program product. In particular, a non-transitory computer-readable recording medium is provided, storing program code portions configured to, when executed by one or more processors, cause the one or more processors to: acquire, for example from a storage unit, data describing a fixed spatial relationship between at least two optically distinguishable lines configured to be detected by an optical detection system of a surgical navigation system simultaneously, wherein the lines are part of a body of an optical tracking device configured to be used in the surgical navigation system, and wherein at least one of the lines is an edge of the body; simultaneously detect the lines; and determine, based on the detected lines and based on the fixed spatial relationship, the spatial position and/or orientation of the optical tracking device.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
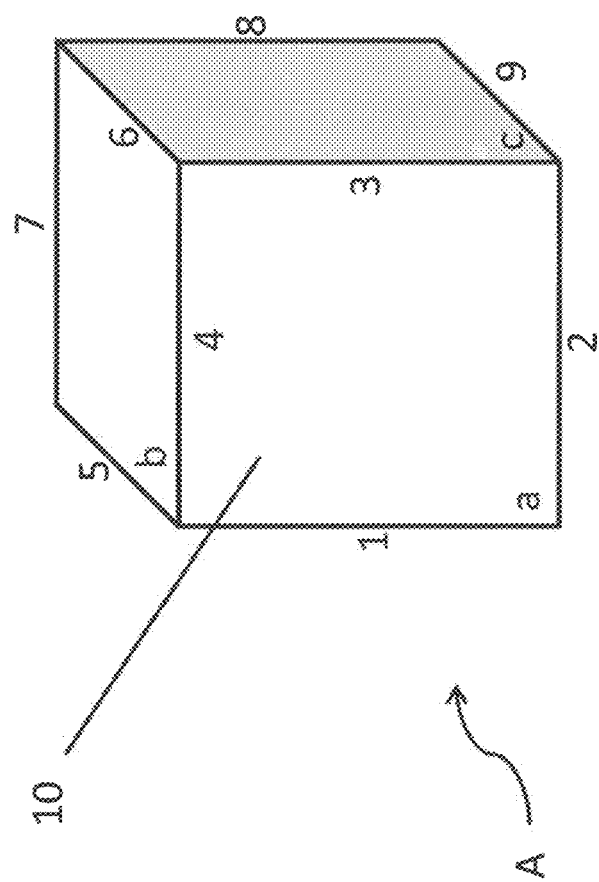
FIG. 1 shows a first embodiment of an optical tracking device.

In the following description, exemplary embodiments of a surgical navigation system and a surgical navigation method will be explained with reference to the drawings. The same reference numerals will be used to denote the same or similar structural features.

FIG. 1 shows a first embodiment of an optical tracking device A comprising a body 10 and optically distinguishable lines 1 to 9. The body 10 is a cube. Lines 1 to 4 which lie on edges of the cube form the boundary of an area "a" which is a side surface of the body 10. Lines 4 to 7 which lie on edges of the cube form the boundary of an area "b" which is another side surface of the body 10. Lines 3, 6, 8 and 9 which lie on edges of the cube form the boundary of an area "c" which is a third side surface of the body 10. For example, in case area "a" is detected due to an illumination intensity higher than that of the lines 1 to 4, the lines 1 to 4 may be detected easily since it is known that these form the boundary of area "a".

The optical tracking device A thus comprises a body 10 which has at least two optically distinguishable lines. In the shown example the body 10 has three optically distinguishable lines 3, 4 and 6 which do not lie in a single plane. The lines all have fixed spatial relationships with respect to one another. In case of lines 3, 4 and 6, at least some, in one example all of the following geometrical relationships are defined a priori as fixed spatial relationships:

The lines 3, 4, and 6 are straight lines with a given length;
Lines 3 and 4 lie in plane "a", lines 3 and 6 lie in plane "c" and lines 4 and 6 lie in plane "b";
Each of the planes is orthogonal to the other two planes;
The angle between lines 3 and 4, lines 4 and 6 and lines 3 and 6, respectively, is equal to 90°;
The lines 3, 4 and 6 have a common intersection point at which the aforementioned angle may be measured.

Figure 2:
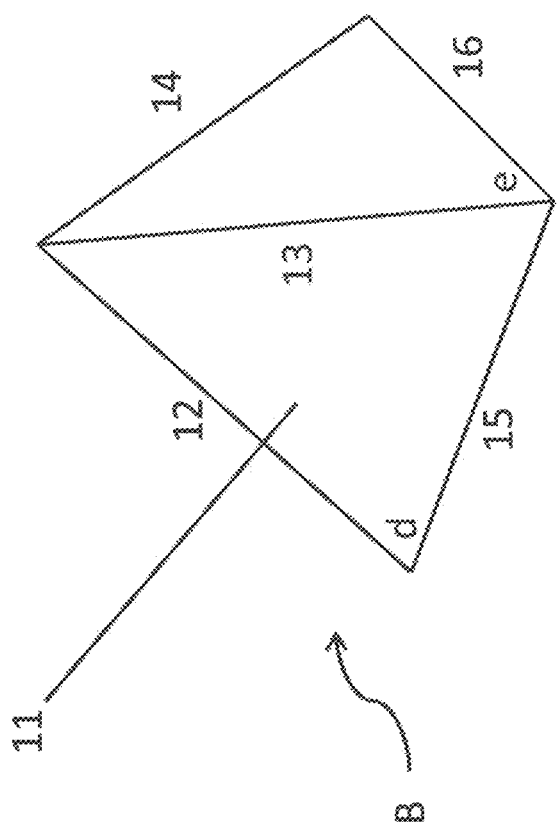
FIG. 2 shows a second embodiment of an optical tracking device.

FIG. 2 shows a second embodiment of an optical tracking device B comprising a body 11 which is a pyramid and optically distinguishable lines 12 to 16 which lie on edges of the pyramid. The body 11 thus has at least two optically distinguishable lines. The lines 12 to 16 do not lie in a single plane. Lines 12, 13 and 15 form the boundary of an area "d" which is a side surface of the body 11. Lines 13, 14 and 16 form the boundary of an area "e" which is another side surface of the body 11.

The optical tracking device B thus comprises a body 11 which has at least two optically distinguishable lines. In the shown example, the body 11 has three optically distinguishable lines 12, 13 and 14 which do not lie in a single plane but in two separate planes. The lines all have fixed spatial relationships with respect to one another. In case of lines 12, 13 and 14, at least some, in one example all of the following geometrical relationships are defined a priori as fixed spatial relationships:

The lines 12, 13 and 14 are straight lines with a given length;
Lines 12 and 13 lie in plane "d" and lines 13 and 14 lie in plane "e";
The three lines have a common intersection point forming the top of the pyramid;
The planes "d" and "e" intersect each other with a first given angle;
The lines 12 and 13 intersect each other with a second given angle and the lines 13 and 14 intersect each other with a third given angle;
Lines 12 and 14 intersect each other with a fourth given angle.

Figure 3:
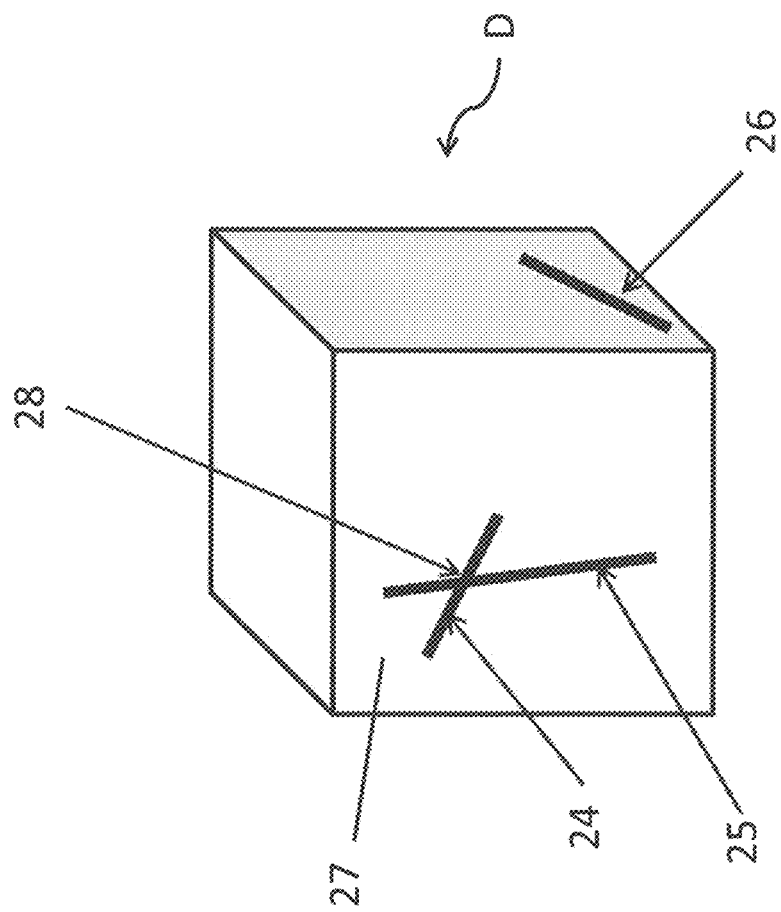
FIG. 3 shows a third embodiment of an optical tracking device.

FIG. 3 shows a third embodiment of an optical tracking device D comprising a body 27 which is a cube and optically distinguishable lines 24 and 25 which lie on a first side surface of the cube. Optically distinguishable line 26 lies on a different side surface of the cube which surface is adjacent to the first side surface. The body 27 may have the form of a pyramid, a cuboid or else comprising a side surface on which the lines 24 and 25 lie and another side surface on which the line 26 lies. The lines 24 and 25 lie in the same plane and intersect one another at intersection point 28.

At least some, in one example all of the following geometrical relationships are defined a priori as fixed spatial relationships:

The line 24 is a straight line with a first given length;
The line 25 is a straight line with a second given length;
The line 26 is a straight line with a third given length;
The lines 24 and 25 intersect one another with a first given angle smaller than 90°;
The lines 24 and 25 intersect one another with a second given angle larger than 90°;
The line 24 is divided by the intersection point 28 into a first segment with a fourth given length and a second segment with a fifth given length;
The line 25 is divided by the intersection point 28 into a first segment with a sixth given length and a second segment with a seventh given length;
The intersection point 28 lies in the same plane as the lines 24 and 25;
The lines 24 and 25 lie in the same plane;
The line 26 lies in a plane which is perpendicular to plane in which lines 24 and 25 lie.

Figure 4:
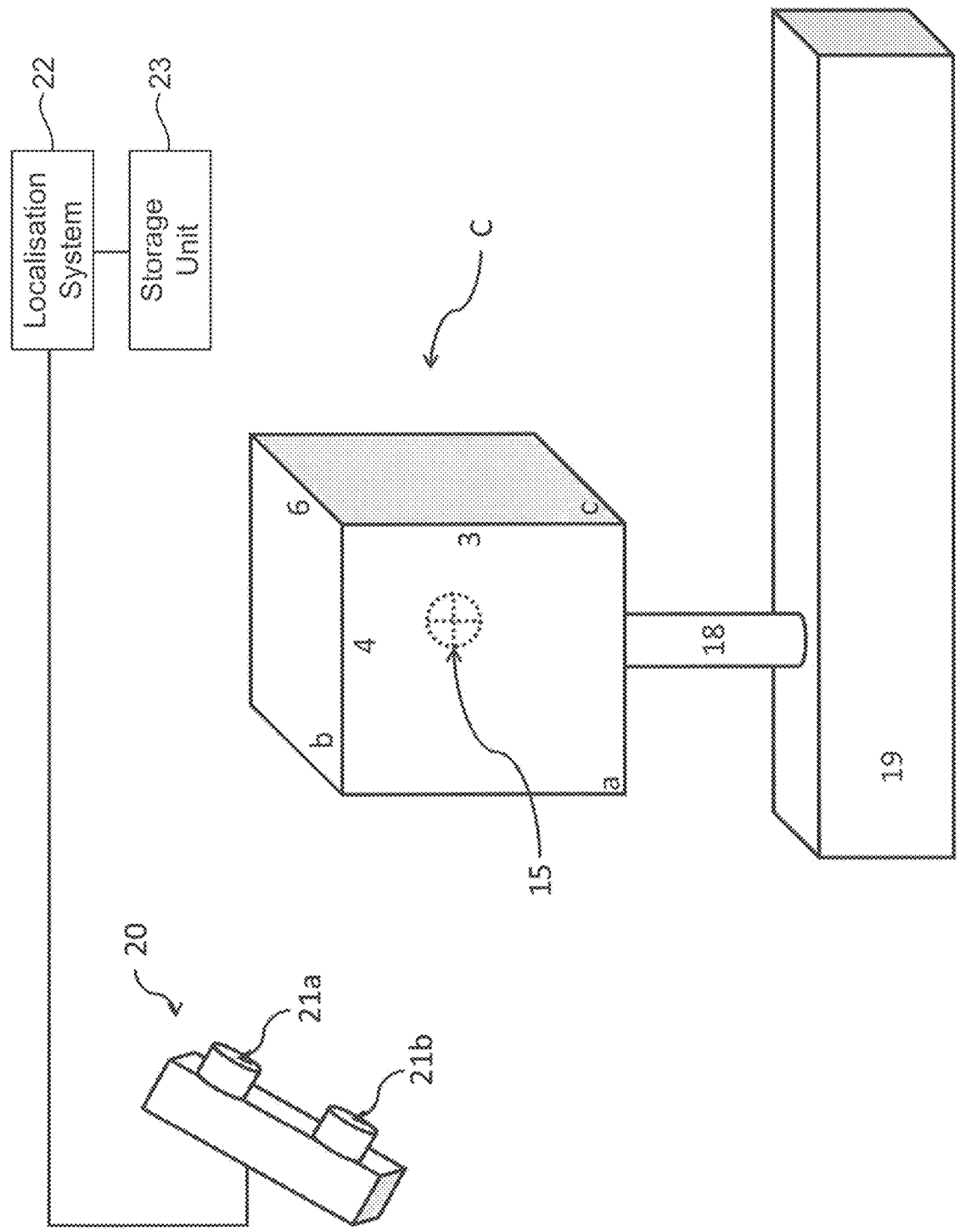
FIG. 4 shows a surgical navigation system comprising an optical tracking device.
Figure 5:
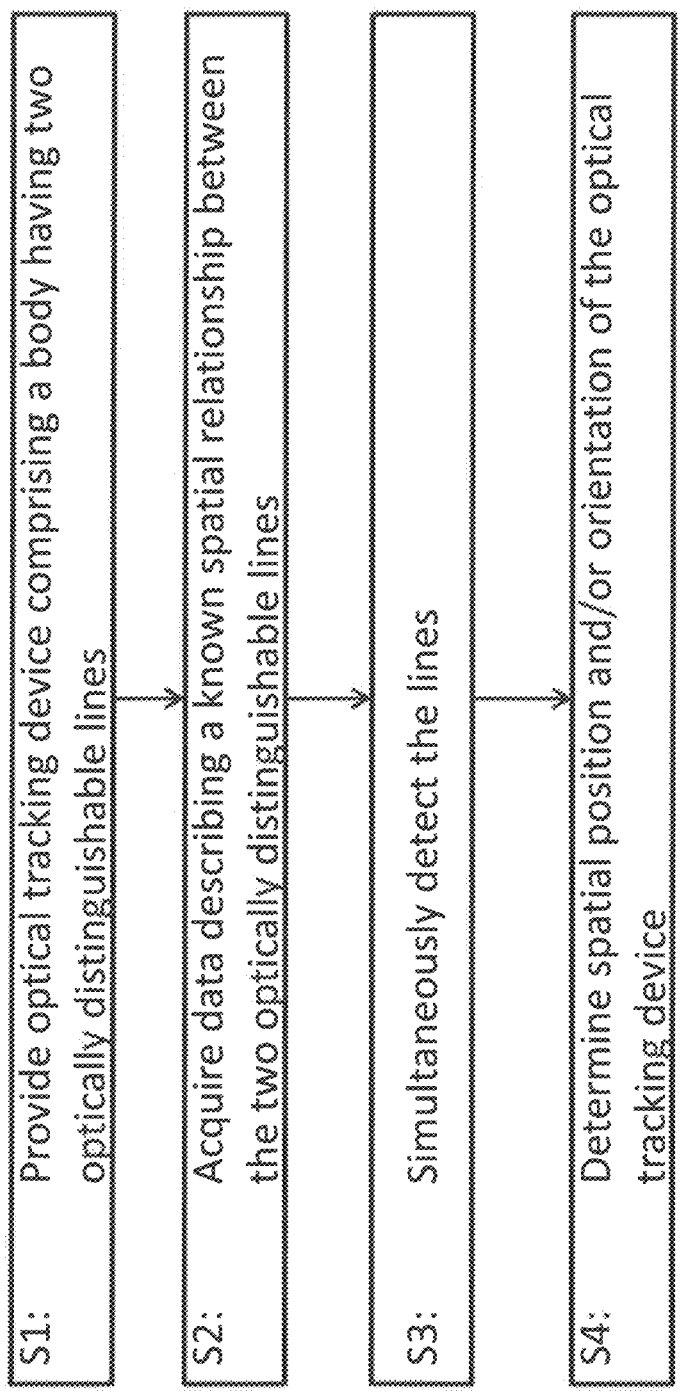
FIG. 5 shows a flow diagram of a surgical navigation method.

FIG. 4 shows a surgical navigation system comprising an optical tracking device C. The optical tracking device C corresponds to the optical tracking device A but includes a light emitting element 17 which is embedded in (the body of) the optical tracking device C. Of course, the body 11 of the optical tracking device C may have a different form, as described for example with reference to FIG. 2. The optical tracking device C is attached to a surgical instrument 19 via a coupling component 18.

For example, the surgical instrument is a needle, a pointer, a chisel, a drill or else. The coupling component 18 ensures a predefined fixed spatial relationship between the optical tracking device C and the surgical instrument. This allows determining the position and/or orientation of the surgical instrument 19 in case the position and/or orientation of the optical tracking device C has been determined.

The surgical navigation system furthermore includes an optical detection device 20 comprising a first optical sensor 21a and a second optical sensor 21b. The optical detection device 20 is for example a stereoscopic camera with a first image sensor and a second image sensor. The camera may be able to detect on or more of optically distinguishable points, lines and areas and is in one example configured to detect multiple optically distinguishable points, lines and/or areas at the same time, for example at least two optically distinguishable lines simultaneously. In case the light emitting element 17 is configured to emit light with a first wavelength (for example in the infrared range), the optical detection device 20 is configured to detect at least light having the first wavelength.

The surgical navigation system furthermore comprises a localisation system 22 and a storage unit 23. The localisation system 22 is configured to determine, based on lines detected by the optical detection device 20 and the fixed spatial relationship between these lines, the spatial position and/or orientation of the optical tracking device C. The storage unit comprises for example a non-transitory recording medium such as a computer-readable recording medium, for example a hard disk or a semiconductor memory. The storage unit 23 may be arranged at a remote location. For example, the storage unit 23 is part of a cloud server or a remote server which is connected to the surgical navigation system via a cable or wirelessly, for example via a network.

In order to detect the lines of the optical tracking device C, these lines have to be optically distinguishable. That is, they have to exhibit a different light emitting behaviour than their surroundings. For example, the lines 3, 4 and 6 emit light whilst the areas a, b and c adjacent to the lines do not emit light or emit light with a lower intensity distinguishable from the intensity emitted by the lines. The light emitting element 17 is in one example configured to emit light selectively via the lines 3, 4 and 6, for example using light-conducting elements or light shielding elements comprised in the light-emitting element which prevent light from being emitted to the areas a, b and c. The optically distinguishable lines may each be formed by a transparent part which enables the light to pass or may be formed as slits in the body's surface. In this example, the lines will appear brighter than the surrounding parts of the body (the areas a, b and c) and may thus be distinguishably detected. Note that the relative position between the optical tracking device C and the optical detection device 20 is not correctly represented in FIG. 4. Of course, the optical detection system has to be able to detect the lines simultaneously. In case the three lines 3, 4 and 6 are to be detected simultaneously, at least a part of each of the three lines 3, 4 and 6 has to be visible to the optical sensors 21a and 21b.

In another example, the light emitting element 17 is configured to emit light selectively to the areas "a", "b" and "c", for example using light-conducting elements or light shielding (blocking) elements comprised in the light emitting element 17 which prevent light from being emitted to the lines 3, 4 and 6. The areas may each be formed by a transparent part which enables the light to pass. In this example, the areas "a", "b" and "c" will appear brighter than the lines 3, 4 and 6 which lie between the areas "a", "b" and "c". The lines will therefore appear with a lower brightness compared to the surrounding areas of the body (the areas a, b and c) and may thus be distinguishably detected since they exhibit a different light emitting behaviour than the surrounding areas. Also in this case, the optical detection system is able to detect at least two optically distinguishable lines simultaneously. In this example, the optical detection system is able to detect the three lines 3, 4 and 6 simultaneously if at least a part of the boundary of each of the three areas "a", "b" and "c", which part touches a line, is visible to the optical sensors 21a and 21b.

In another example, the light emitting element 17 is configured to emit light to some of the areas "a", "b", "c" and to some of the lines 3, 4 and 6. For example, light emitting element 17 is configured to emit light to area "a" and to line 6. In this case, line 6 appears brighter than its neighbouring areas "b" and "c" and may thus be detected reliably. Lines 3 and 4 may be detected by detecting area "a" and interpolating the four detected linear outline segments. The result of the interpolation is four straight lines which lie in plane "a". Afterwards, the straight lines which meet in an intersection point common with detected line 6 may be chosen as lines 3 and 4. That is, the fixed spatial relationship between the three lines 3, 4 and 6 is used in detecting the lines. Other combinations of illuminated lines and areas are also possible as long as at least two lines are detected. Also, in case only parts of an illuminated line are detected such as points which lie on the line, interpolation may be used to determine a straight line representing the line. Instead or in addition to interpolation, extrapolation techniques may be applied in order to detect the lines. For example, a part of an outline of area "a" may be detected to be straight. The straight part may then be used to extrapolate a straight line with infinite length which may represent a line.

The light emitting element 17 may be configured to emit light to lines but not to corners of the body 10, 11. For example, the lines of the body 10, 11 are made of an opaque or non-transparent material whilst the lines are made of a transparent material and the light emitting element is embedded in the body 10, 11 and configured to emit light to the lines. For example, the light emitting element emits light via an optical fibre comprised in the light emitting element to a line. In this case, the optical fibre might run along the line and emit light at one or more side portions of the fibre. The fibre may be the optical fibre "12" described in European patent application 19153075.7. The light emitting element 17 may be configured to emit other combinations of areas and lines of the optical tracking device C. The body 10 of the optical tracking device C may have the form of body 11 or another geometrical form.

The light emitting element 17 may emit light with a different wavelength to different parts of the body 10 or light with different intensities. These values might also be varied during time resulting in a temporal pattern which may be associated with an individual line or area or to distinguish a line from an area. For example, the areas "a", "b" and "c" might emit blue light whilst the lines 3, 4 and 6 emit red light or IR light. The lines 3, 4 and 6 might emit light for 100 ms periodically whilst the areas "a", "b" and "c" might emit light for 10 ms periodically.

FIG. 4 shows a flow diagram of a surgical navigation method. In step S1, an optical tracking device is provided. The optical tracking device may be the optical tracking device A, B or C described above. The optical tracking device comprises a body having at least two optically distinguishable lines.

In step S2, data is acquired describing a fixed spatial relationship between the at least two optically distinguishable lines. The data may be acquired from a storage device such as the storage device 23.

In step S3, the lines of the optical tracking device are detected simultaneously, for example by an optical detection device such as the optical detection device 20 described above. In on variant, at least two of the at least two optically distinguish-able lines are detected simultaneously. In another variant, all of the optically distinguishable lines are detected simultaneously. The lines may be detected taking into account the fixed spatial relationship described by the acquired data as described above.

In step S4, the spatial position and/or orientation of the optical tracking device is determined based on the detected lines and the fixed spatial relationship described by the acquired data, for example by a localisation system such as the localisation system 22 described above.

In particular, in case of a single interpolated and/or extrapolated straight line obtained during the detecting step S3, only one dimensional constraint can be deducted, namely that one line has to lie on the straight line. In case of two interpolated and/or extrapolated straight lines obtained during the detecting step S3, at least two dimensional constraints can be deducted, namely that one line has to lie on a straight line and another line has to lie on the other one. In this case, in which only two lines are detected, the spatial position and/or orientation of the optical tracking device can only be determined decisively without ambiguity if the length of at least one of the lines is also detected during detecting the line. Of course, the length of each line, the angle of intersection between the lines (if the lines intersect one another), the length of a line segment formed by the intersection point may be determined upon detecting the lines. Alternatively, an additional line may be detected in order to avoid such ambiguity. Generally speaking, in case more parameters of the lines—such as line length, segment length, intersection angle, common plane in which the line lies together with another line—are obtained upon detecting the lines, more of these can be compared with the predetermined geo-metrical relationships in order to avoid detection of unwanted elements. Also, the number of possible positions and/or orientations of the optical tracking device which would result in the same detected line parameters can be minimized in case more parameters of the lines are obtained. This enables a more precise determination of the spatial position and/or orientation of the optical tracking device by minimizing ambiguity.

Of course, detection of additional lines may be used in order to minimize ambiguity. For example, in case a third interpolated and/or extrapolated straight line is also obtained in the detecting step S3, a third dimensional constraint may be deducted, namely that a third line has to lie on this line. In case the lines do not lie in a single plane, the spatial position of the optical tracking device A, B, C can then be determined decisively.

Depending on the fixed spatial relationship between the at least two optically distinguishable lines, the spatial orientation may also be determined decisively. In order to determine the spatial orientation, namely the rotational components describing the spatial orientation of the optical tracking device, in some cases further information might be required. For example, in case of the body 10 of the optical tracking device A having the form of a cube and the lines 3, 4 and 6 being three lines which intersect at one of the cube's corners, three different rotational orientations are possible resulting in the same line detection result.

An additional line may be detected to prevent such ambiguity. In the example of the cube, two lines 3 and 4 which intersect one another at a corner of the cube may be detected and a further line such as line 5 which is orthogonal to line 3 and line 4 and does not touch the intersection point. Alternatively or additionally, the lines may be configured to be distinguishable from one another, for example by emitting different light signals. Alternatively or additionally, the lines may have an asymmetrical geometrical relationship such as different lengths and/or different intersection angles to prevent this ambiguity. In this case, the body may have an asymmetrical form.

The method may further comprise repeating steps S3 and S4 in order to enable time-dependent tracking of the optical tracking device which may be useful in surgery.

The invention claimed is:

1. An optical tracking device configured to be used in a surgical navigation system, the optical tracking device comprising:
    a body having at least two optically distinguishable lines configured to be detected by an optical detection system of the surgical navigation system simultaneously, wherein the lines have a fixed spatial relationship between each other and at least one of the lines is an edge of the body, and wherein the lines do not lie in a single plane; and
    at least one light emitter disposed in the body and configured to illuminate a first of the lines and a surface area of the body having at least one of the lines as a boundary,
    wherein the at least one light emitter is configured to illuminate the first line to exhibit a first light emitting behavior and illuminate the surface area to exhibit a second light emitting behavior different from the first light emitting behavior, and
    wherein the first light emitting behavior differs from the second light emitting behavior in temporal pattern of emitted light such that a first temporal light pattern of the first light emitting behavior is anticyclic to a second temporal light pattern of the second light emitting behavior.

2. The optical tracking device of claim 1, wherein all of the lines are edges of the body.

3. The optical tracking device according claim 1, wherein the light emitter is configured to illuminate only a part of at least one of the lines.

4. The optical tracking device according to claim 3, wherein the light emitter is configured to illuminate all at least one of the lines completely.

5. The optical tracking device according to claim 1, wherein the surface area is covered with an optically transparent filter so that a light intensity of the surface area is less than a light intensity of at least one of the lines.

6. The optical tracking device according to claim 1, wherein at least one of the lines forms a curve.

7. The optical tracking device according to claim 1, wherein at least two of the lines touch one another.

8. The optical tracking device according to claim 2, wherein the body is a cube.

9. A surgical navigation system comprising:
    an optical tracking device comprising:
        a body having at least two optically distinguishable lines, wherein the lines have a fixed spatial relationship between each other, and each of the lines is an edge of the body, and at least one light emitter disposed in the body and configured to illuminate a first of the lines and a surface area of the body having a second of the lines as boundary, wherein the first and second lines do not lie in a single plane,
        wherein the at least one light emitter is configured to illuminate the first line to exhibit a first light emitting behavior and illuminate the surface area to exhibit a second light emitting behavior, the first light emitting behavior differing from the second light emitting behavior in temporal pattern of emitted light such that a first temporal light pattern of the first light emitting behavior is anticyclic to a second temporal light pattern of the second light emitting behavior;
    an optical detection system configured to detect the lines of the optical tracking device from the illumination of the first line and the surface area, wherein the lines of the optical tracking device are configured to be detected by the optical detection system simultaneously; and
    one or more processors configured to determine a spatial position and/or orientation of the optical tracking device based on the detected lines and based on the fixed spatial relationship between the at least two optically distinguishable lines.

10. The surgical navigation system according to claim 9, wherein the one or more processors are configured to acquire data describing the fixed spatial relationship from a storage unit.

11. A surgical navigation method of determining a spatial position and/or orientation of an optical tracking device, comprising:
    providing an optical tracking device comprising a body and at least one light emitter disposed in the body, the body having at least two optically distinguishable lines, wherein each of the lines is an edge of the body, the lines do not lie in a single plane, and the at least one light emitter is configured to illuminate a first of the lines to exhibit a first light emitting behavior and illuminate a surface area of the body to exhibit a second light emitting behavior, the surface area having a second of the lines as boundary, and the first light emitting behavior differing from the second light emitting behavior in temporal pattern of emitted light such that a first temporal light pattern of the first light emitting behavior is a nticyclic to a second temporal light pattern of the second light emitting behavior;

acquiring data describing a fixed spatial relationship between the lines; simultaneously detecting the lines from the illumination of the surface area and the first line; and determining, based on the detected lines and based on the fixed spatial relationship, the spatial position and/or orientation of the optical tracking device.

12. The surgical navigation method according to claim 11, wherein the at least one light emitter is configured to illuminate only a part of the first line, and the step of detecting the lines comprises:

detecting the illuminated part of the first line; and extrapolating and/or interpolating the detected illuminated part to detect the first line.

13. The surgical navigation method according to claim 11, wherein the surface area has only a part of the second line as a boundary, and the step of detecting the lines comprises:

detecting the illuminated surface area having the part of the second line as a boundary; and extrapolating and/or interpolating the boundary of the surface area to detect the second line.

14. The optical tracking device according to claim 1, wherein the lines do not have the same lengths.

15. The optical tracking device according to claim 1, wherein the surface area of the body is defined as a first planar surface area of the body, theft first line, a second of the lines, and a third of the lines each forms a different edge of the body, the first and third lines bound a second planar surface area of the body, and the second and third lines bound the first planar surface area of the body.

16. The surgical navigation system according to claim 9, wherein the surface area of the body is defined as a first planar surface area of the body, the first line and a third of the lines bound a second planar surface area of the body, and the second and third lines bound the first planar surface area of the body.

17. The optical tracking device according to claim 15, wherein an intersection of the first line, second, and third lines forms a corner of the body.

18. The optical tracking device according to claim 16, wherein an intersection of the first line, second, and third lines forms a corner of the body.

19. The surgical navigation system according to claim 9, wherein the at least one light emitter is configured to illuminate only a part of the first line, and the optical detection system is configured to detect the lines of the optical tracking device from the illumination of the first line by being configured to detect the illuminated part of the first line and extrapolate and/or interpolate the detected illuminated part to the first line.

* * * * *